United States Patent
Fleming et al.

(10) Patent No.: US 7,220,260 B2
(45) Date of Patent: May 22, 2007

(54) ELECTROSURGICAL SYSTEM

(75) Inventors: Alistair I. Fleming, Cardiff (GB); Huw L Jones, Llantrisant (GB)

(73) Assignee: Gyrus Medical Limited, Cardiff (GB)

( * ) Notice: Subject to any disclaimer, the term of this patent is extended or adjusted under 35 U.S.C. 154(b) by 108 days.

(21) Appl. No.: 10/464,778

(22) Filed: Jun. 19, 2003

(65) Prior Publication Data

US 2004/0002745 A1 Jan. 1, 2004

Related U.S. Application Data

(60) Provisional application No. 60/402,555, filed on Aug. 12, 2002.

(30) Foreign Application Priority Data

Jun. 27, 2002 (GB) .................................. 0214907.8

(51) Int. Cl.
*A61B 18/18* (2006.01)
(52) U.S. Cl. .................... 606/39; 128/898; 606/41; 606/48
(58) Field of Classification Search ............... 128/898; 606/32–50
See application file for complete search history.

(56) References Cited

U.S. PATENT DOCUMENTS

| 4,043,342 | A | * | 8/1977 | Morrison, Jr. ................ 606/48 |
| 4,674,498 | A | | 6/1987 | Stasz |
| 4,706,667 | A | | 11/1987 | Roos |
| 4,850,353 | A | | 7/1989 | Stasz et al. |
| 4,862,889 | A | * | 9/1989 | Feucht .......................... 606/32 |
| 4,862,890 | A | | 9/1989 | Stasz et al. |
| 4,958,539 | A | | 9/1990 | Stasz et al. |
| 5,300,068 | A | * | 4/1994 | Rosar et al. ................... 606/34 |
| 5,370,645 | A | * | 12/1994 | Klicek et al. ................. 606/35 |
| 5,423,809 | A | * | 6/1995 | Klicek .......................... 606/38 |
| 5,496,312 | A | * | 3/1996 | Klicek .......................... 606/34 |
| 5,514,129 | A | | 5/1996 | Smith |
| 5,540,684 | A | * | 7/1996 | Hassler, Jr. ................... 606/40 |
| 5,599,344 | A | * | 2/1997 | Paterson ....................... 606/34 |
| 5,860,975 | A | * | 1/1999 | Goble et al. .................. 606/45 |
| 5,871,481 | A | * | 2/1999 | Kannenberg et al. ......... 606/34 |
| 6,083,223 | A | * | 7/2000 | Baker ........................... 606/52 |
| 6,093,186 | A | * | 7/2000 | Goble ........................... 606/34 |
| 6,296,636 | B1 | | 10/2001 | Cheng et al. |
| 6,648,883 | B2 | * | 11/2003 | Francischelli et al. ......... 606/41 |
| 6,832,998 | B2 | * | 12/2004 | Goble ........................... 606/48 |
| 2003/0004507 | A1 | * | 1/2003 | Francischelli et al. ......... 606/41 |

FOREIGN PATENT DOCUMENTS

| GB | 2 164 473 A | 3/1986 |
| WO | WO 93/08757 | 5/1993 |
| WO | WO 99/20213 | 4/1999 |

\* cited by examiner

*Primary Examiner*—Henry M Johnson, III
(74) *Attorney, Agent, or Firm*—Oliff & Berridge, PLC

(57) ABSTRACT

An electrosurgical system comprises a generator and an instrument including a first electrode, a second electrode, and an insulating spacer separating the first and second electrodes. The generator repeatedly measures a characteristic of the radio frequency output such as the impedance between the first and second electrodes. The generator analyses the impedance measurements, and interrupts the radio frequency signal when the rate of change of the impedance is such as to indicate the onset of a "flare-out". In this way, the power is reduced before the flare-out leads to permanent damage or failure of the instrument.

2 Claims, 3 Drawing Sheets

ELECTROSURGICAL SYSTEM

This nonprovisional application claims the benefit of U.S. Provisional Application No. 60/402,555, filed Aug. 12, 2002. The entire disclosure of the prior application is hereby incorporated by reference herein in its entirety.

FIELD OF THE INVENTION

This invention relates to an electrosurgical system, and in particular to one in which an electrosurgical generator provides a radio frequency (RF) cutting signal to a bipolar surgical instrument.

BACKGROUND OF THE INVENTION

A typical bipolar cutting instrument, which may also be capable of tissue coagulation, comprises first and second electrodes separated by an insulating spacer. An early example of a bipolar RF cutting device is U.S. Pat. No. 4,706,667 issued to Roos, in which the return or "neutral" electrode is set back from the active electrode. In a series of patents (including U.S. Pat. No. 4,674,498, U.S. Pat. No. 4,850,353, U.S. Pat. No. 4,862,890 and U.S. Pat. No. 4,958,539) Stasz proposed a variety of cutting blade designs. These were designed with relatively small gaps between two electrodes such that arcing would occur therebetween when an RF signal was applied to the blade, the arcing causing the cutting of the tissue. In an alternative arrangement, described in co-pending British Patent Application No. 0130975.6 and U.S. patent application Ser. No. 10/105,811, a device is provided in which the spacing of the electrodes is designed such that direct arcing between the electrodes does not occur, but arcing does occur between one of the electrodes and the tissue at the target site.

Normal use of this instrument has proved very satisfactory, but in exceptional circumstances (especially where the instrument has been used in an overly aggressive manner) a situation hereinafter referred to as a "flare-out" may develop. It is not uncommon for small particles of condensed tissue and other debris to become attached to the electrodes, and ordinarily this poses no particular problem. However, in the case of a flare-out, the debris forms a conductive track between the electrodes, allowing current to flow directly therebetween. This low impedance electrical pathway from one electrode to the other, if allowed to continue for a period of several seconds, may conduct sufficient current that a failure of the device may occur. This may be by way of a failure of the insulating material forming the spacer, either by the insulating material experiencing such high temperatures that it becomes conductive, or by the temperature differentials throughout the insulator causing a physical cracking of the material. Alternatively, the extreme temperatures caused by the current flow may produce a physical melting of the electrode material itself.

SUMMARY OF THE INVENTION

The present invention provides a way in which this condition, although rarely occurring, can be prevented from causing a failure of the device. Accordingly, there is provided an electrosurgical system including an RF generator, an electrosurgical instrument comprising at least first and second electrodes and an insulating spacer separating the first and second electrodes, the RF generator being adapted to supply an RF signal between the first and second electrodes, means for measuring a characteristic of the output of the RF generator, and a controller adapted to analyse the measured characteristic and change the RF signal supplied between the first and second electrodes when an aspect of the characteristic meets a predetermined criterion indicating the onset of a "flare-out".

Conveniently, the characteristic of the output of the RF generator which is measured is the voltage across the first and second electrodes, or alternatively the current flowing therebetween. It has been discovered that there are a number of criteria which may indicate the onset of a flare-out. These include rapid changes in the impedance experienced between the electrodes, leading to large and sudden changes in the voltage between the electrodes or the current flowing therebetween. There may be an increase in the number or amplitude of high frequency components of the current or voltage signal, or an increase in the D.C. thermionic current sensed between the electrodes. In a preferred arrangement, the predetermined criterion indicating the onset of a flare-out is the changeability of the measured characteristic, typically the rate of change of the impedance between the electrodes, or the changeability as represented by the sum of the differences between successive impedance measurements.

Preferably, the controller is adapted to change the RF signal by reducing the power thereof when the predetermined criteria indicating the onset of a flare-out is met. Alternatively, the controller may reduce the voltage of the radio frequency signal, or even the frequency thereof. Where the RF signal comprises a signal having dual components at a first and second frequency, the controller may change the signal by adjusting the relative proportions of the first and second frequency components. Preferably, however, the controller is adapted to reduce the power of the RF signal, and may reduce it substantially to zero when the characteristic meets the predetermined criterion. Conveniently, the power is reduced substantially to zero for a period of at least 5 seconds, allowing time for the instrument to be withdrawn from the surgical site and the electrodes to be cleaned if necessary. Alternatively the power is reduced to zero until the operator of the instrument manually resets the instrument.

In one convenient arrangement, the controller is adapted to reduce the power of the RF signal supplied between the first and second electrodes only when the aspect of the characteristic meets the predetermined criterion for a predetermined period of time. This serves to ensure that false detection of a flare-out is not triggered by a transient change in the measured characteristic. The system may require a series of repeated measurements of the characteristic to all fit the predetermined criterion before action is taken.

Although potentially of use with other types of instrument, the present invention is primarily designed to be employed with instruments in which the first and second electrodes and the insulating spacer are such that the spacing between the electrodes is between 0.25 mm and 3.0 mm.

According to one preferred construction, an electrosurgical system includes a radio frequency generator, an electrosurgical instrument comprising at least first and second electrodes and an insulating spacer separating the first and second electrodes, the radio frequency generator being adapted to supply a radio frequency signal between the first and second electrodes, means for measuring the impedance between the first and second electrodes, and a controller adapted to analyse the impedance measurements and interrupt the radio frequency signal supplied between the first and second electrodes when the changeability of the impedance exceeds a predetermined threshold value.

The invention further resides in an electrosurgical generator for supplying radio frequency power to an electrosurgical instrument which includes at least first and second electrodes, the radio frequency generator including a radio frequency output stage having at least a pair of RF output lines for connection to the first and second electrodes respectively, a power supply coupled to the output stage for supplying power to-the output stage, and a controller capable of varying the RF signal applied to the RF output lines, wherein there are provided means for measuring a characteristic of the radio frequency signal across the output lines, the controller being adapted to analyse the measured characteristic and change the radio frequency signal supplied to the output stage when an aspect of the characteristic meets a predetermined criterion indicating the onset of a "flare-out".

More specifically, the present invention relates to an electrosurgical generator for supplying radio frequency power to an electrosurgical instrument which includes at least first and second electrodes, the radio frequency generator including a radio frequency output stage having at least a pair of RF output lines for connection to the first and second electrodes respectively, a power supply coupled to the output stage for supplying power to the output stage, and a controller capable of varying the RF signal applied to the RF output lines, wherein there are provided means for measuring the impedance across the output lines, the controller being adapted to analyse the impedance measurements and interrupt the radio frequency signal supplied to the output stage when the changeability of the impedance exceeds a predetermined threshold value.

The present invention also extends to a method of cutting tissue at a target site comprising providing a bipolar cutting blade comprising first and second electrodes and an electrical insulator spacing apart the electrodes, bringing the blade into position with respect to the target site such that one electrode is in contact with tissue at the target site and the other is adjacent thereto, supplying an electrosurgical voltage to the cutting blade such that arcing does not occur in air between the first and second electrodes but that arcing does occur between one of the electrodes and the tissue at the target site, measuring the impedance between the first and second electrodes, and interrupting the electrosurgical voltage when the changeability of the impedance exceeds a predetermined threshold value.

Finally, according to another aspect of the invention, an electrosurgical system comprises an RF generator having a pair of output terminals, and an electrosurgical instrument having a bipolar electrode assembly in the form of first and second electrodes adjacent each other and insulated from each other by a spacer, the electrodes being connectible to the output terminals, wherein the generator includes means for generating a monitoring signal representative of an electrical parameter associated with signals developed across the electrodes, and a controller responsive to the monitoring means to change the radio frequency signal supplied by the generator to the instrument when the monitoring signal meets a predetermined criterion indicative of the onset of flare-out. Typically, the predetermined criterion is the variability of the electrical parameter on the monitoring signal reaching or exceeding a predetermined level. In the preferred generator, the electrical parameter is the load impedance across the generator output terminals and the controller is arranged to generate the sum of the differences between successive samples of the monitoring signal taken over a predetermined measurement period as a representation of the variability of the parameter.

The present invention will now be further described below, by way of example only, with reference to the accompanying drawings.

DETAILED DESCRIPTION OF THE PREFERRED EMBODIMENT

Figure 1:
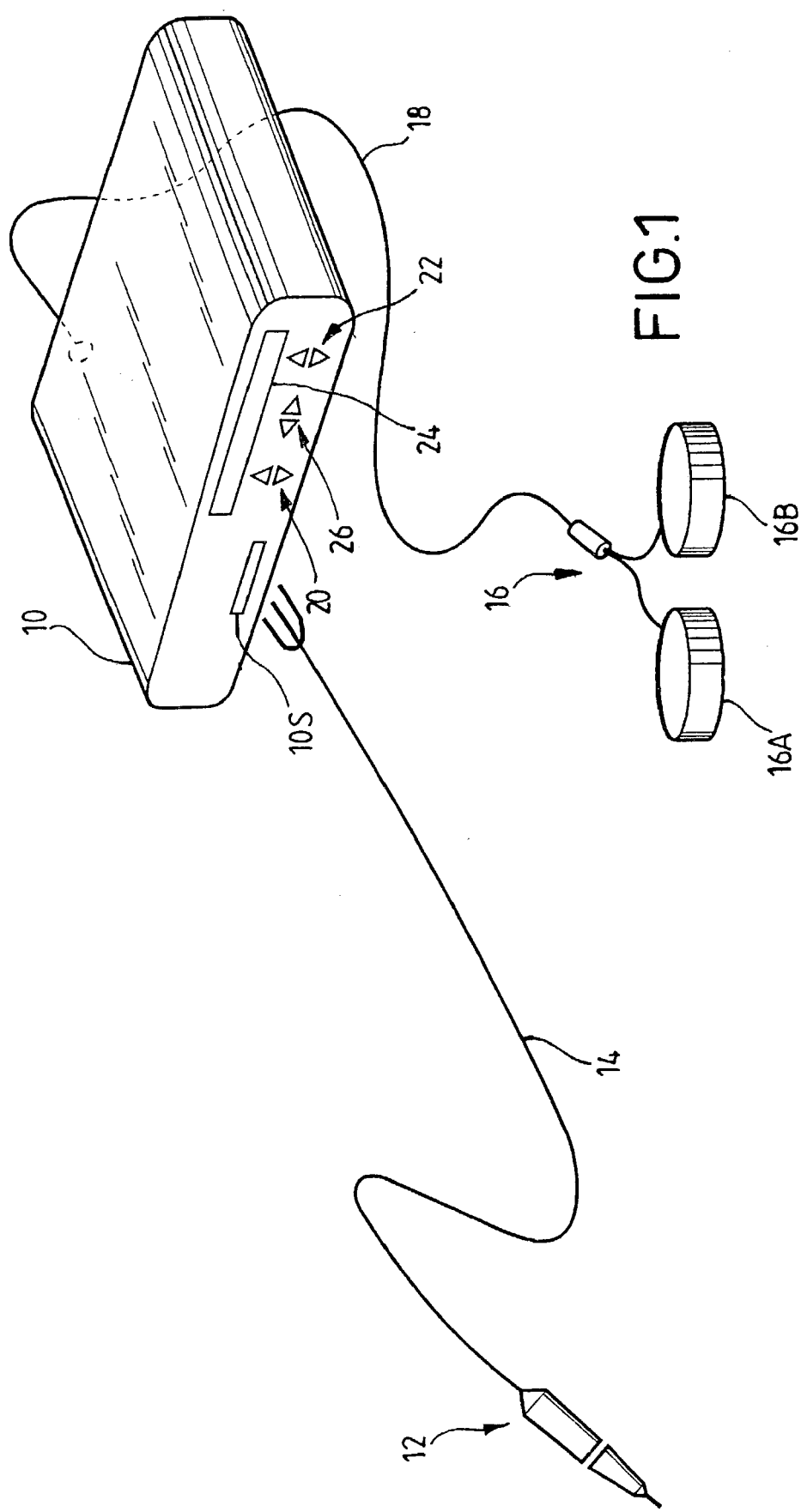
FIG. 1 is a schematic diagram of an electrosurgical system in accordance with the present invention.

Referring to FIG. 1, a generator 10 has an output socket 10S providing an RF output for an instrument 12 via a connection cord 14. Activation of the generator may be performed from the instrument 12 via a connection in cord 14 or by means of a footswitch unit 16, as shown, connected to the rear of the generator by a footswitch connection cord 18. In the illustrated embodiment footswitch unit 16 has two footswitches 16A and 16B for selecting a coagulation mode and a cutting mode of the generator respectively. The generator front panel has push buttons 20 and 22 for respectively setting coagulation and cutting power levels, which are indicated in a display 24. Push buttons 26 are provided as an alternative means for selection between coagulation and cutting modes.

Figure 2:
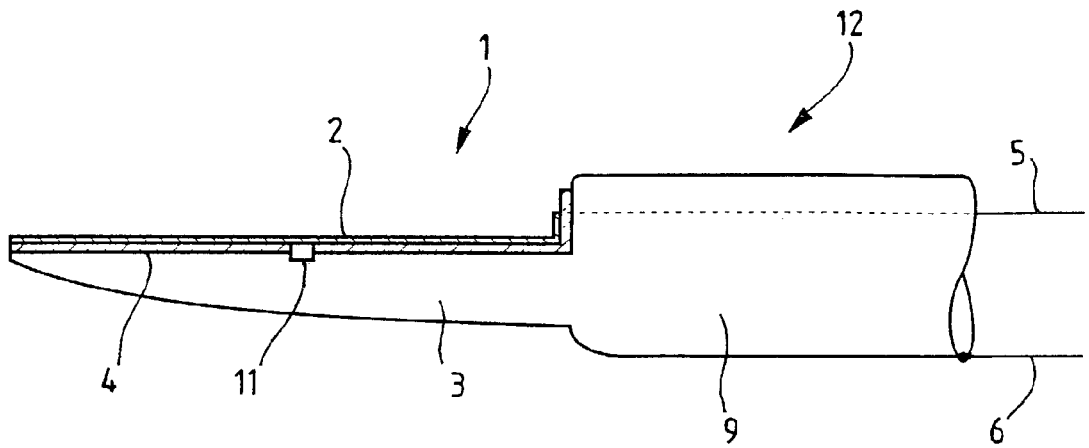
FIG. 2 is a schematic side view of an electrosurgical instrument suitable for use in the system of FIG. 1.

Referring to FIG. 2, the instrument 12 comprises a blade shown generally at 1 and including a generally flat first electrode 2, a larger second electrode 3 and an electrical insulator 4 separating the first and second electrodes. The first electrode 2 is formed of stainless steel while the second electrode 3 is formed from copper integrally with a body portion 9. The surface of the second electrode is plated with a biocompatible material such as stainless steel, or alternatively with a non-oxidising material such as gold, platinum or palladium. The electrical insulator 4 is formed from a ceramic material such as $Al_2O_3$.

A conductive lead 5 is connected to the first electrode 2, while another conductive lead 6 is connected to the second electrode 3. The RF output from the generator 10 is connected to the blade 1 via the leads 5 and 6 so that a radio frequency signal having a substantially constant peak voltage (typically around 400V) appears between the first and second electrodes. When the blade 1 is brought into contact with tissue at a target site, the RF voltage causes arcing between one of the electrodes and the tissue surface. Because the first electrode 2 is smaller in cross-sectional area, and has a lower thermal capacity and conductivity than that of the second electrode 3, the first electrode assumes the role of the active electrode and arcing occurs from this electrode to the tissue. Electrical current flows through the tissue to the second electrode 3, which assumes the role of the return electrode. Cutting of the tissue occurs at the active electrode, and the blade may be moved through the tissue.

Figure 3:
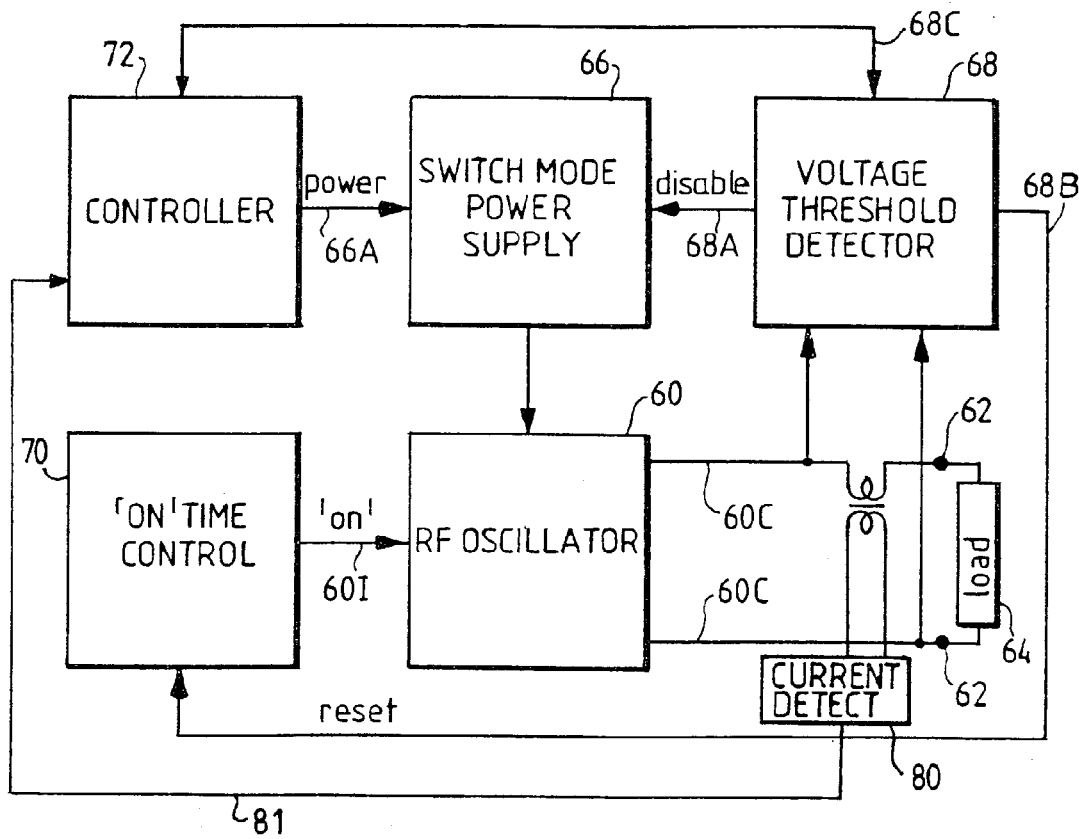
FIG. 3 is a schematic block diagram of the generator of the system of FIG. 1, and FIGS. 4 and 5 are schematic representations of the voltage, current and impedance measured across the electrodes of the system of FIG. 1, in normal operation and in the event of a flare-out, respectively.

Referring to FIG. 3, the generator comprises an RF power oscillator 60 having a pair of output lines 60C for coupling via output terminals 62 to the load impedance 64 represented by the instrument 12 when in use. Power is supplied to the oscillator 60 by a switched mode power supply 66.

In the preferred embodiment, the RF oscillator 60 operates at about 400 kHz, with any frequency from 300 kHz upwards into the HF range being feasible. The switched mode power supply typically operates at a frequency in the range of from 25 to 50 kHz. Coupled across the output lines 60C is a voltage threshold detector 68 having a first output 68A coupled to the switched mode power supply 16 and a second output 68B coupled to an "on" time control circuit 70. A microprocessor controller 72 coupled to the operator controls and display (shown in FIG. 1) is connected to a control input 66A of the power supply 66 for adjusting the generator output power by supply voltage variation and to a threshold-set input 68C of the voltage threshold detector 68 for setting peak RF output voltage limits. Also coupled across the output lines 60C is a current detection circuit 80 which feeds signals to the controller 72 via line 81.

In operation, the microprocessor controller 72 causes power to be applied to the switched mode power supply 66 when electrosurgical power is demanded by the surgeon operating an activation switch arrangement which may be provided on a hand-piece or footswitch (see FIG. 1). A constant output voltage threshold is set independently on the supply voltage via input 68C according to control settings on the front panel of the generator (see FIG. 1). Typically, for desiccation or coagulation the threshold is set at a desiccation threshold value between 150 volts and 200 volts. When a cutting or vaporisation output is required the threshold is set to a value in the range of from 250 or 300 volts to 600 volts. These voltage values are peak values. Their being peak values means that for desiccation at least it is preferable to have an output RF waveform of low crest factor to give maximum power before the voltage is clamped at the values given. Typically a crest factor of 1.5 or less is achieved.

When the generator is first activated, the status of the control input 60I of the RF oscillator 60 (which is connected to the "on" time control circuit 70) is "on", such that the power switching device which forms the oscillating element of the oscillator 60 is switched on for a maximum conduction period during each oscillation cycle. The power delivered to the load 64 depends partly on the supply voltage applied to the RF oscillator 60 from the switched mode power supply 66 and partly on the load impedance 64. The voltage threshold for a desiccation output is set to cause trigger signals to be sent to the "on" time control circuit 70 and to the switched mode power supply 66 when the voltage threshold is reached. The "on" time control circuit 70 has the effect of virtually instantaneously reducing the "on" time of the RF oscillator-switching device. Simultaneously, the switched mode power supply is disabled so that the voltage supplied to oscillator 60 begins to fall. The operation of the generator in this way is described in detail in our European Patent Application No. 0754437, the disclosure of which is hereby incorporated by way of reference.

Referring back to FIG. 2, when the instrument 12 is in use, small particles of condensed tissue and other debris can become adhered to the edge electrode 2 and, to a lesser extent, the base electrode 3. If the instrument is used particularly aggressively, it is possible that a conductive track of such debris can build up between the electrodes 2 and 3 across the ceramic insulator 4. Such a conductive track is shown schematically at 11 in FIG. 2. If no action is taken to prevent it, this conductive track 11 develops into a "flare-out" in which the current passing directly between the electrode 2 and the electrode 3 will cause the instrument to overheat and finally fail. The following description explains how the generator 10 detects and compensates for just such a situation.

Figure 4:
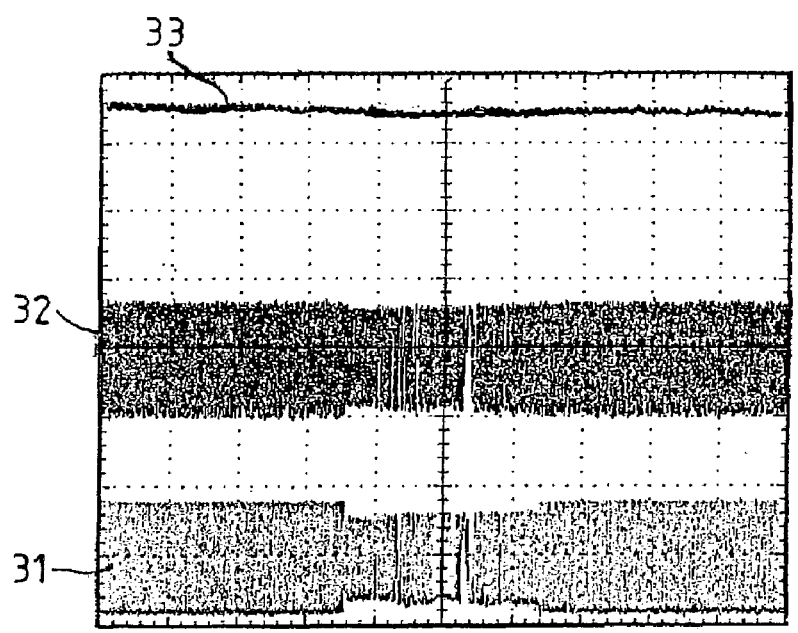

At regular intervals, in this case every 10 ms the current is measured across the load 64 by the current detector 80 and the current value is sent to the controller 72. The controller uses the current value to determine repeatedly the impedance across the load 64. The difference between successive impedance values, irrespective of their absolute value, is calculated, and summed for 16 consecutive readings to give a first total $Z_1$. The current measurements continue every 10 ms until a further 16 consecutive impedance calculations have been made, which calculations are again summed to give a second total $Z_2$. If $Z_1$ and $Z_2$ are both less than the threshold criteria for the sum Q of the impedance changes, then the generator continues to supply RF signals to the instrument 12. The process is continued with further current measurements being sent to the controller 72 every 10 ms. This normal operation is shown in FIG. 4, in which the voltage across the electrodes 2, 3 is shown by trace 31, the current flowing by trace 32 and the impedance measured by the generator by trace 33.

Figure 5:
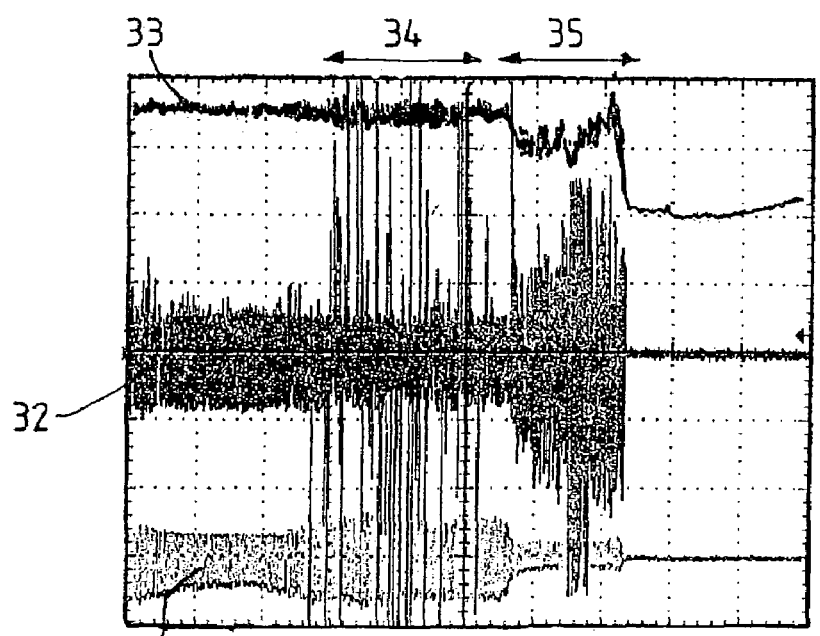

If a flare-out starts to develop between the electrodes 2 and 3, the current measured across the load 64 will start to fluctuate widely, and with a high frequency of oscillation. This is shown in FIG. 5, with the build up to the flare-out being shown at 34 and the onset of the flare-out at 35. In these circumstances $Z_1$ and $Z_2$ (representing differences in impedance values, not absolute impedance values) will both be above the threshold for the sum Q of the impedance changes, and this causes the controller to send a signal to the power supply 66 to cause the power to be interrupted. A typical value for Q is 1000 ohms, for a 16-measurement cycle.

In addition to interrupting the power supply, the controller may cause a message (such as "Clean Tip") to be displayed by the display 24. The controller does not allow power to be restored to the output of the generator until the surgeon has pressed a reset button to indicate that the tip has been cleaned, and will repeat the interruption process if the impedance measurements show that the flare-out conditions are still in existence when the power is recommenced.

It will be appreciated that criteria other than the changeability of the impedance across the output of the generator could be employed to give an indication of the onset of a flare-out. These include, non-exhaustively, the high frequency content (e.g. the number of high frequency components) of the modulation of the current or voltage signal, or the D.C. thermionic current flowing between the electrodes 2 and 3. The latter will be measured in the manner disclosed in U.S. Pat. No. 6,547,786, the contents of which are incorporated herein by reference.

It will also be appreciated that, while the embodiments of the invention have been described with reference to the elimination of flare-outs, the invention could in some aspects be used to prevent overheating of electrodes without the actual existence of a flare-out. The generator, detecting that a criterion indicating the start of a potential overheating situation has been met, could reduce the power or alter the radio frequency signal in other ways so as to maintain operation of the electrosurgical system within proper parameters. Those skilled in the art of electrosurgical generators will readily be able to establish suitable detection criteria to keep the generator operating within safe and effective limits.

What is claimed is:

1. A method of cutting tissue at a target site, comprising:
i) providing a bipolar cutting blade comprising first and second electrodes and an electrical insulator spacing apart the electrodes,
ii) bringing the blade into position with respect to the target site such that one electrode is in contact with tissue at the target site and the other is adjacent thereto,
iii) supplying an electrosurgical voltage to the cutting blade such that arcing does not occur in air between the first and second electrodes but that arcing does occur between one of the electrodes and the tissue at the target site, the voltage supplied, capable of vaporising tissue,
iv) repeatedly measuring the impedance between the first and second electrodes,
v) calculating the difference between successive impedance measurements,
vi) summing the calculated difference values for a predetermined number of impedance difference calculations to obtain a total value, and
vii) interrupting the electrosurgical voltage when the total value exceeds a predetermined threshold value.

2. A method of cutting tissue at a target site, comprising:
i) providing a bipolar cutting blade comprising first and second electrodes and an electrical insulator spacing apart the electrodes,
ii) bringing the blade into position with respect to the target site such that one electrode is in contact with tissue at the target site and the other electrode in contact with tissue is adjacent to the tissue at the target site,
iii) supplying an electrosurgical voltage to the cutting blade such that arcing does not occur in air between the first electrode and the second electrode and arcing does occur between one of the electrodes and the tissue at the target site, the voltage supplied capable of vaporizing tissue,
iv) repeatedly measuring the impedance between the first electrode and the second electrode,
v) calculating the difference between successive impedance measurements,
vi) summing the calculated differences for a predetermined number of the calculated differences to obtain a first total value,
vii) summing the calculated differences for a further predetermined number of the calculated differences to obtain a second total value, and
viii) interrupting the electrosurgical voltage when both the first total value and the second total value exceed a predetermined threshold value.

* * * * *